(12) United States Patent
Park et al.

(10) Patent No.: US 10,118,298 B2
(45) Date of Patent: Nov. 6, 2018

(54) LOWER BODY SUPPORTING ROBOT SYSTEM AND CONTROL METHOD THEREOF

(71) Applicant: HYUNDAI MOTOR COMPANY, Seoul (KR)

(72) Inventors: Sang In Park, Suwon-si (KR); Kyung Mo Jung, Seongnam-si (KR); Dong Jin Hyun, Suwon-si (KR); Hyun Seop Lim, Anyang-si (KR)

(73) Assignee: HYUNDAI MOTOR COMPANY, Seoul (KR)

( * ) Notice: Subject to any disclaimer, the term of this patent is extended or adjusted under 35 U.S.C. 154(b) by 188 days.

(21) Appl. No.: 15/342,336

(22) Filed: Nov. 3, 2016

(65) Prior Publication Data

US 2017/0354518 A1 Dec. 14, 2017

(30) Foreign Application Priority Data

Jun. 9, 2016 (KR) ........................ 10-2016-0071798

(51) Int. Cl.
*B25J 13/08* (2006.01)
*B25J 9/00* (2006.01)
(Continued)

(52) U.S. Cl.
CPC ........... *B25J 13/089* (2013.01); *B25J 9/0006* (2013.01); *A61F 2002/704* (2013.01);
(Continued)

(58) Field of Classification Search
CPC ........ B25J 9/0006; B25J 13/089; A61H 3/00; A61H 2201/165; A61H 2003/007;
(Continued)

(56) References Cited

U.S. PATENT DOCUMENTS 8,375,484 B2 2/2013 Ota et al.
2007/0273320 A1* 11/2007 Shishido .............. B25J 19/0091
318/568.12

(Continued)

FOREIGN PATENT DOCUMENTS

JP 2012-030077 A 2/2012
JP 2014-184083 A 10/2014
(Continued)

OTHER PUBLICATIONS

Office Action issued in corresponding Korean Patent Application No. 10-2016-0071798, dated Aug. 16, 2017.

*Primary Examiner* — Dale Moyer
(74) *Attorney, Agent, or Firm* — McDermott Will & Emery LLP

(57) ABSTRACT

A lower body supporting robot system includes a lower body mechanism being worn on a user's lower body, the lower body mechanism including a plurality of joints and links and a drive device, a distance calculator for measuring a first distance that is a vertical distance to an object located therebelow and a second distance that is a vertical distance to a ground surface, a memory for storing a limit distance that is a vertical distance between the distance calculator and the ground surface when the lower body mechanism is in a lowest sitting posture, and a controller for calculating a tolerance distance that is a difference between the second distance and the limit distance, comparing the first distance with the tolerance distance, and controlling the drive device so that the distance calculator moves by the first distance when the first distance is less than the tolerance distance.

12 Claims, 6 Drawing Sheets

(51) Int. Cl.
 *B25J 11/00* (2006.01)
 *A61F 2/70* (2006.01)
(52) U.S. Cl.
 CPC .............. *A61H 2201/165* (2013.01); *A61H 2201/5069* (2013.01); *A61H 2201/5071* (2013.01); *B25J 11/009* (2013.01); *G05B 2219/40305* (2013.01)
(58) Field of Classification Search
 CPC .... A61H 2201/1652; A61H 2201/5058; G05B 2219/40305
 See application file for complete search history.

(56) References Cited

U.S. PATENT DOCUMENTS

| | | | |
|---|---|---|---|
| 2012/0023661 A1 | 2/2012 | Ota et al. | |
| 2013/0110015 A1 | 5/2013 | Ota et al. | |
| 2015/0088269 A1* | 3/2015 | Roh | A61F 2/72 623/25 |
| 2016/0296404 A1 | 10/2016 | Ota et al. | |
| 2018/0064357 A1* | 3/2018 | Motoyama | A61B 5/04012 |

FOREIGN PATENT DOCUMENTS

| | | |
|---|---|---|
| JP | 5773718 B2 | 9/2015 |
| KR | 10-0716597 B1 | 5/2007 |
| KR | 10-2015-0034405 A | 4/2015 |
| WO | 2015/011837 A1 | 1/2015 |

\* cited by examiner

LOWER BODY SUPPORTING ROBOT SYSTEM AND CONTROL METHOD THEREOF

CROSS-REFERENCE TO RELATED APPLICATION

This application claims the benefit of priority to Korean Patent Application No. 10-2016-0071798, filed on Jun. 9, 2016 with the Korean Intellectual Property Office, the disclosure of which is incorporated herein by reference.

TECHNICAL FIELD

The present disclosure relates to a lower body supporting robot system, which is worn by a user who has paraplegia or other lower body disabilities in order to support movement of the lower body, which assists the user in stably sitting on an object in a sitting mode, and which is advantageous to secure the safety of the user without causing the user inconvenience by minimizing errors during a control operation, and a control method thereof.

BACKGROUND

A wearable robot for a paraplegic patient serves to assist the patient who cannot use their lower body in walking. When such a robot performs a sitting motion, the sitting motion is a predetermined motion. However, because the height of a sitting target object may change in various situations, there is a risk of the robot performing an unstable motion, which makes it unlikely to secure the safety of a wearer.

The wearable robot is generally controlled, for example, to assist walking by measuring the distance between the soles and the ground surface, or to issue a warning or to be limited in driving by measuring the distance to an external object when the robot moves.

However, a concept in which, in order to control the case where the wearer attempts to sit, any object behind the robot is accurately detected such that the robot is automatically controlled based on the result of detection, has not been proposed. Such a concept would thereby realize a stable sitting mode under various situations in which the robot maintains the balance thereof so as to secure the safety of the user.

Therefore, with regard to the lower body supporting robot described above, there is a demand for the development of a technology that detects an object behind the robot, and allows the robot to accurately and stably perform a sitting motion based on the result of the detection.

The matters disclosed in this section are merely for enhancement of understanding of the general background of the disclosure and should not be taken as an acknowledgment or any form of suggestion that the matters form the related art already known to a person skilled in the art.

SUMMARY

Therefore, the present disclosure has been made in view of the above problems, and it is an object of the present disclosure to provide a lower body supporting robot system, which is worn by a user who has paraplegia or other lower body disability in order to support movement of the lower body, which assists the user in stably sitting on an object in a sitting mode, and which is advantageous to secure the safety of the user without causing the user inconvenience by minimizing errors during a control operation, and a control method thereof.

In accordance with an aspect of the present disclosure, the above and other objects can be accomplished by the provision of a lower body supporting robot system including a lower body mechanism being worn on the user's lower body, the lower body mechanism including a plurality of joints and links, and a drive device, a distance calculator provided above the lower body mechanism for calculating a measurement distance that is a vertical distance to an object located therebelow, and a location distance that is a vertical distance to a ground surface, a memory for storing a limit distance that is a vertical distance between the distance calculator and the ground surface when the lower body mechanism is in a lowest sitting posture, and a controller for calculating a tolerance distance that is a difference between the location distance and the limit distance, comparing the measurement distance with the tolerance distance, and controlling the drive device of the lower body mechanism so that the distance calculator moves by the measurement distance when the measurement distance is less than the tolerance distance. In the lower body mechanism, the links may include a calf link and a thigh link, the joints may include an ankle joint, a knee joint, and a hip joint, and the drive device may include one or more drive devices for adjusting angles of the respective joints.

The distance calculator may include a distance sensor and an angle sensor, the distance sensor may measure a spacing distance to the object located therebelow, and the angle sensor may measure a tilt angle between the distance sensor and the ground surface, and the distance calculator may calculate the measurement distance that is a vertical distance between the distance sensor and the object located therebelow using the spacing distance and the tilt angle.

The distance sensor may measure a ground surface distance to the ground surface, and the distance calculator may calculate the location distance that is the vertical distance between the distance sensor and the ground surface using the ground surface distance and the tilt angle.

The distance calculator may calculate the location distance in a mechanical manner using lengths of the respective links and angles of the respective joints of the lower body mechanism.

The memory may store a motion rule of the drive device to be performed in a sitting mode, and the controller may control the drive device according to the motion rule when the lower body mechanism performs a sitting mode, and may control the drive device so that the distance calculator moves by the measurement distance when the measurement distance is less than the tolerance distance.

The controller may control the drive device of the lower body mechanism so that the distance calculator moves by the tolerance distance when the measurement distance is greater than the tolerance distance.

The distance calculator may include a plurality of distance sensors, and may calculate measurement distances using the respective distance sensors, the controller may select a smallest measurement distance among the measurement distances, may compare the smallest measurement distance with the tolerance distance, and may control the drive device of the lower body mechanism so that the distance calculator moves by the smallest measurement distance when the smallest measurement distance is less than the tolerance distance.

In accordance with another aspect of the present disclosure, there is provided a method of controlling a lower body supporting robot system, including calculating a measurement distance that is a vertical distance between a distance calculator and an object located therebelow, calculating a location distance that is a vertical distance between the distance calculator and a ground surface, calculating, by a controller, a tolerance distance that is a difference between the location distance and a limit distance, and comparing, by the controller, the measurement distance with the tolerance distance, and controlling a drive device of a lower body mechanism so that the distance calculator moves by the measurement distance when the measurement distance is less than the tolerance distance.

In the step of calculating the measurement distance, a spacing distance to the object located therebelow may be measured using a distance sensor, and a tilt angle between the distance sensor and the ground surface may be measured using an angle sensor, whereby the measurement distance that is a vertical distance between the distance sensor and the object located therebelow may be calculated using the spacing distance and the tilt angle.

In the step of calculating the location distance, a ground surface distance to the ground surface may be measured using the distance sensor, whereby the location distance that is the vertical distance between the distance sensor and the ground surface may be calculated using the ground surface distance and the tilt angle.

In the step of calculating the location distance, the location distance may be calculated in a mechanical manner using lengths of respective links and angles of respective joints of the lower body mechanism.

BRIEF DESCRIPTION OF THE DRAWINGS

The above and other objects, features and other advantages of the present disclosure will be more clearly understood from the following detailed description taken in conjunction with the accompanying drawings, in which.

DETAILED DESCRIPTION

Figure 1:
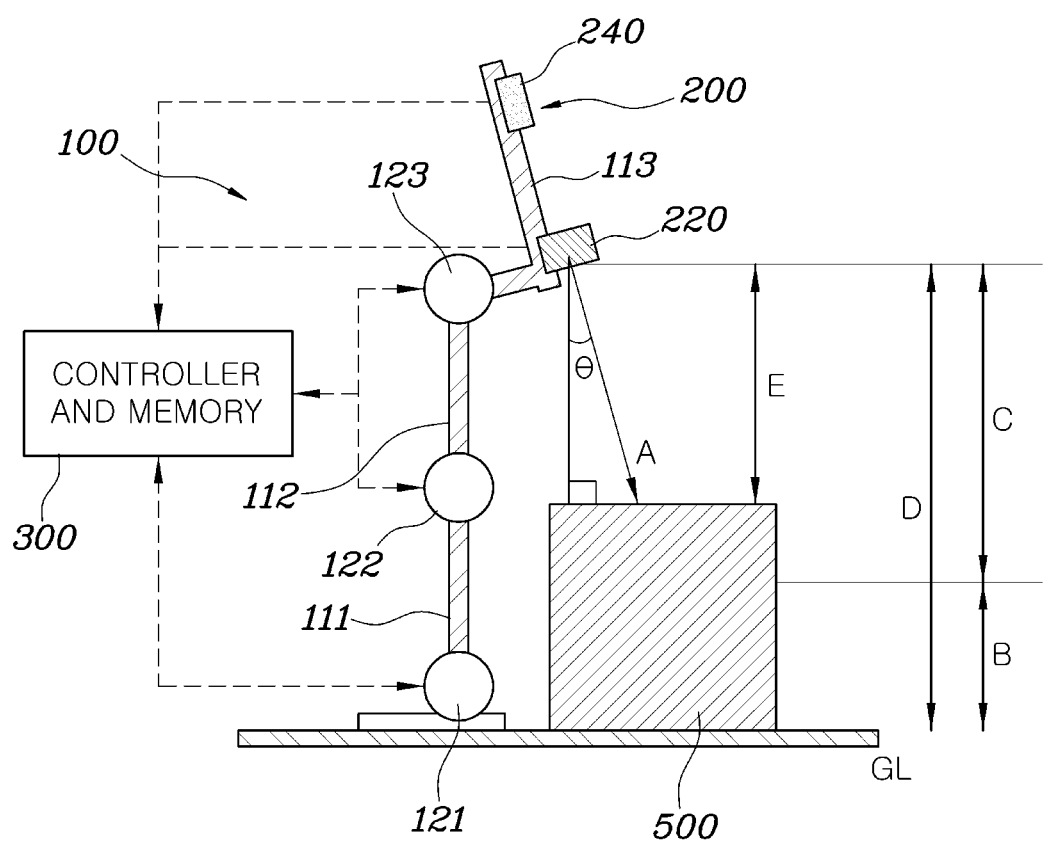
FIG. 1 is a view illustrating a lower body supporting robot system according to an exemplary embodiment of the present disclosure.
Figure 2:
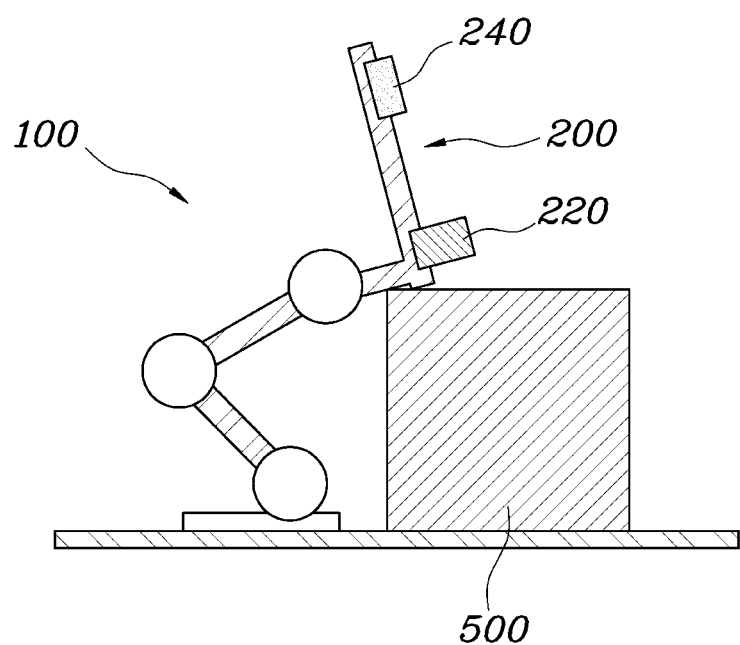
FIG. 2 is a view illustrating a sitting mode of the lower body supporting robot system illustrated in FIG. 1.
Figure 3:
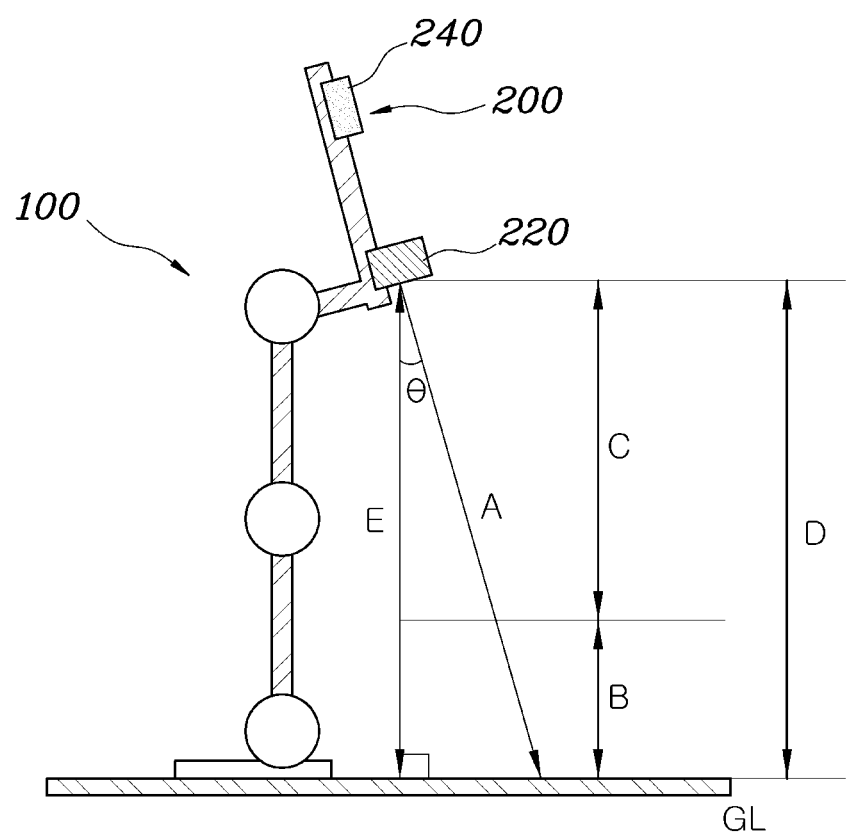
FIGS. 3 and 4 are views illustrating other sitting modes of the lower body supporting robot system illustrated in FIG. 1.
Figure 4:
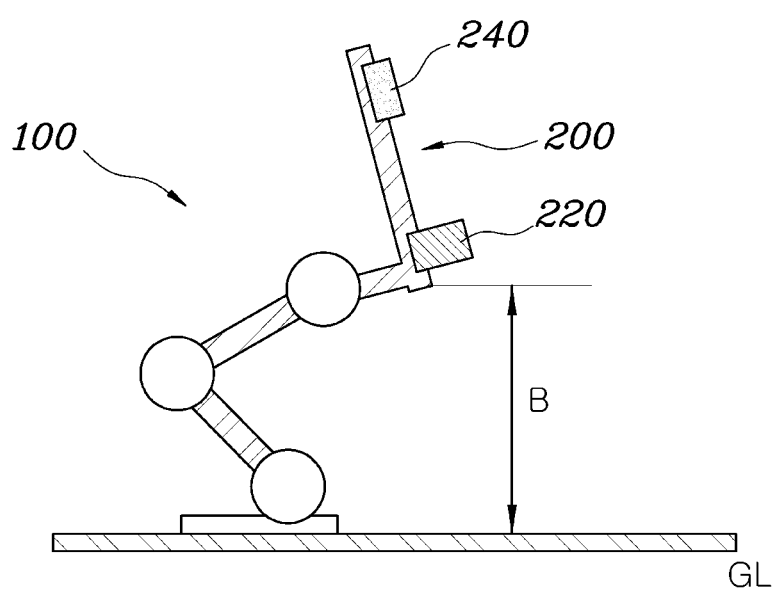
Figure 5:
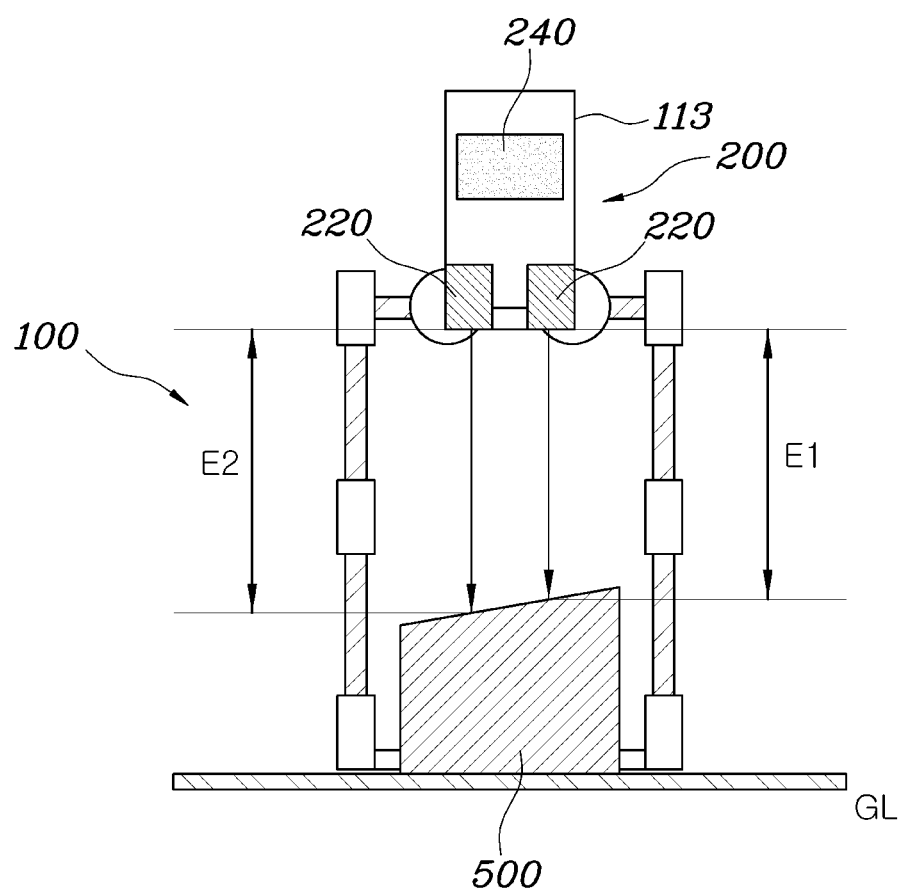
FIG. 5 is a view illustrating a sitting mode of the lower body supporting robot system illustrated in FIG. 1 for an inclined object.
Figure 6:
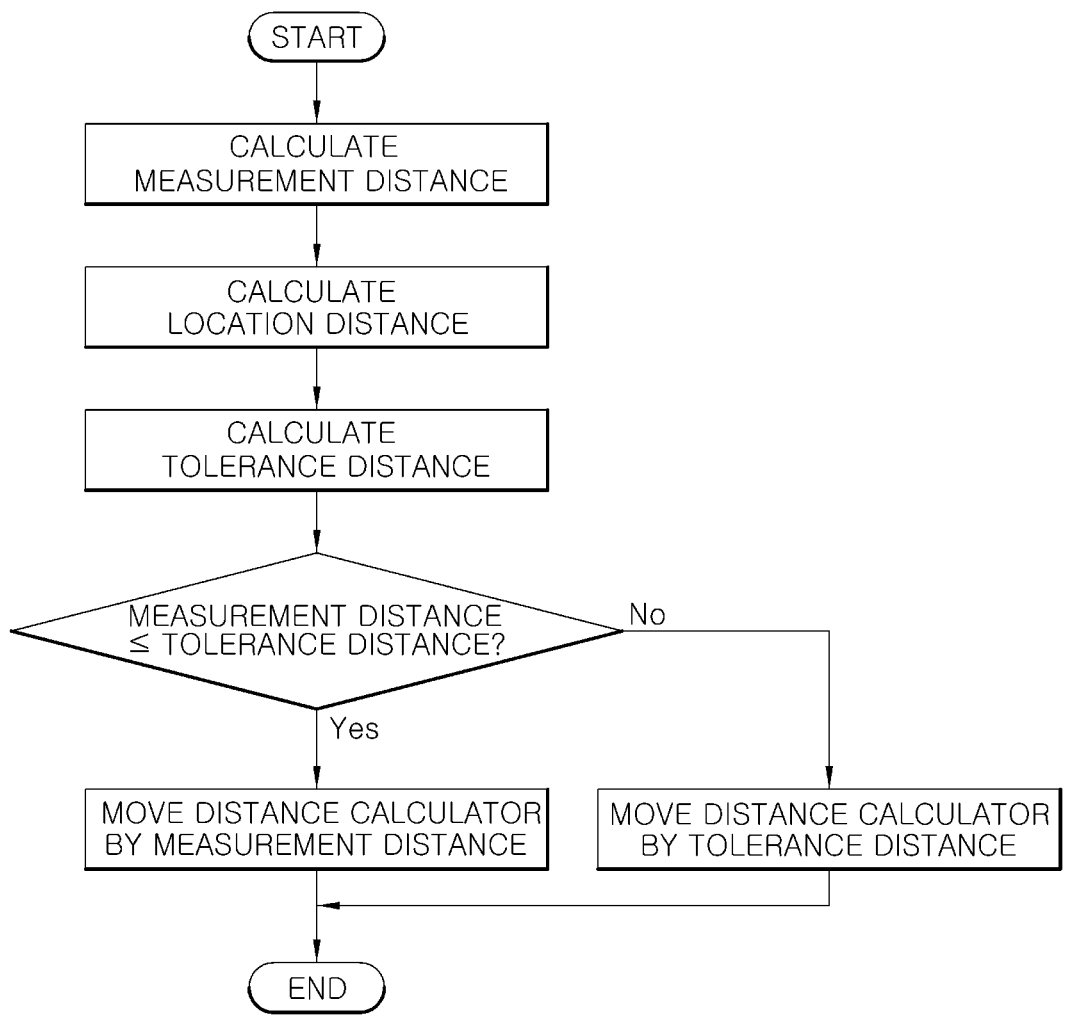
FIG. 6 is a flowchart illustrating a control method of the lower body supporting robot system illustrated in FIG. 1.

FIG. 1 is a view illustrating a lower body supporting robot system according to an exemplary embodiment of the present disclosure, FIG. 2 is a view illustrating a sitting mode of the lower body supporting robot system illustrated in FIG. 1, FIGS. 3 and 4 are views illustrating other sitting modes of the lower body supporting robot system illustrated in FIG. 1, FIG. 5 is a view illustrating a sitting mode of the lower body supporting robot system illustrated in FIG. 1 for an inclined object, and FIG. 6 is a flowchart illustrating a control method of the lower body supporting robot system illustrated in FIG. 1.

The lower body supporting robot system according to an embodiment of the present disclosure includes a lower body mechanism 100, which is worn on the user's lower body and is provided with a plurality of joints and links and one or more drive devices, and a distance calculator 20 provided above the lower body mechanism 100 and calculating a measurement distance E, which is the vertical distance to an object 500 located therebelow and a location distance D, which is the vertical distance to a ground surface GL. The lower body supporting robot system may also include a memory 300, which stores a limit distance B, which is the vertical distance between the distance calculator 200 and the ground surface GL when the lower body mechanism 100 is in the lowest sitting posture, and a controller 300, which calculates a tolerance distance C, which is the difference between the location distance D and the limit distance B, compares the measurement distance E with the tolerance distance C, and controls the drive devices of the lower body mechanism 100 so that the distance calculator 200 may move by the measurement distance E when the measurement distance E is less than the tolerance distance C.

The present disclosure relates to the lower body mechanism 100, which is worn on the user's lower body and is provided with the joints and links and the drive devices. The lower body mechanism 100, as illustrated in FIG. 1, is provided with the joints and links, and the drive devices may be motors integrated with the respective joints. Only one motor may be provided so that the joints cooperate with one another via wires, or hydraulic devices or the like may be used instead of the motors.

The lower body mechanism 100, which is worn on the user's lower body as described above, assists the user who is paralyzed in the lower body during walking or sitting via driving thereof.

Accordingly, the present disclosure may have the configuration illustrated in FIG. 1. FIG. 1 is a view illustrating a lower body supporting robot system according to an exemplary embodiment of the present disclosure, in which a base 113 is provided above the lower body mechanism 100 so as to support the user's waist. The distance calculator 200 may be provided on the base 113. The distance calculator 200 may calculate the measurement distance E, which is the vertical distance to the object 500, which is placed on the bottom, i.e. the ground surface GL behind the user. In addition, the distance calculator 200 calculates the location distance D, which is the vertical distance to the ground surface GL. That is, the distance calculator 200 calculates the vertical distance from the distance calculator 200 to the object 500 and the vertical distance from the distance calculator 200 to the ground surface GL, and the respective vertical distances are referred to as the measurement distance E and the location distance D.

Meanwhile, the memory 300 may store the limit distance B, which is the vertical distance between the distance calculator 200 and the ground surface GL when the lower body mechanism 100 is in the lowest sitting posture. The limit distance B refers to the vertical distance to the ground surface GL when the lower body mechanism 100 is crouched down to the maximum extent. Although the limit distance B may change depending on the physical structure of the lower body mechanism 100, a specific limit distance B may be stored as a characteristic value with respect to a specific lower body mechanism 100. The limit distance B means that the lower body mechanism 100 cannot sit down lower than the limit distance B.

In addition, the controller 300 is provided. The controller 300 may control the drive devices of the lower body mechanism 100, and exchange information with respective sensors and memories. The controller 300 calculates the tolerance distance C, which is the difference between the location distance D and the limit distance B, compares the measurement distance E with the tolerance distance C, and controls the drive devices of the lower body mechanisms 100 so that the distance calculator 200 may move by the measurement distance E when the measurement distance E is less than the tolerance distance C.

That is, when the limit distance B is subtracted from the location distance D, which is the distance between the distance calculator 200 and the ground surface GL, the result gives the maximum distance by which the distance calculator 200 can lower for sitting, and is defined as the tolerance distance C. The controller 300 first calculates the tolerance distance C. Then, the controller 300 compares the tolerance distance C with the measurement distance E, which is the actual distance by which the distance calculator 200 needs to move downward for sitting.

When the measurement distance E is less than the tolerance distance C, the lower body mechanism 100 may sit on the object 500 in a sitting mode illustrated in FIG. 2. FIG. 2 is a view illustrating a sitting mode of the lower body supporting robot system illustrated in FIG. 1. The object 500 illustrated in FIG. 1 has a mechanically sufficient height to allow the lower body mechanism 100 to stably sit on the upper end thereof as illustrated in FIG. 2. Accordingly, in such a state, the controller 300 compares the measurement distance E with the tolerance distance C, and controls the drive devices of the lower body mechanism 100 so that the distance calculator 200 may move by the measurement distance E when the measurement distance E is less than the tolerance distance C.

Specifically, in the lower body mechanism 100, the links may include a calf link 111 and a thigh link 112, the joints may include an ankle joint 121, a knee joint 122 and a hip joint 123, and the drive devices may adjust the angles of the respective joints.

In addition, the memory 300 may store motion rules of the drive devices to be performed in a sitting mode, and the controller 300 may control the drive devices according to the motion rules when the lower body mechanism 100 performs a sitting mode. Thereby, the drive devices of the lower body mechanism 100 are driven to rotate the links, thus realizing a sitting mode illustrated in FIG. 2. With regard to the realization of the sitting mode, a final target destination may become the measurement distance E, and a sitting motion ends when the lower body mechanism 100 sits down by the measurement distance E, in other words, when the distance calculator 200 reaches the upper end of the object 500.

Meanwhile, the distance calculator 200 may include a distance sensor 220 and an angle sensor 240, as illustrated in FIG. 1. The distance sensor 220 may measure a spacing distance A to the object 500 located therebelow, and the angle sensor 240 may measure a tilt angle θ between the distance sensor 220 and the ground surface GL. The distance calculator 200 may calculate the measurement distance E, which is the vertical distance between the distance sensor 220 and the object 500 located therebelow using the spacing distance A and the tilt angle θ. The distance sensor 220 included in the distance calculator 200 may be a sensor using, for example, ultrasonic waves or lasers, and the angle sensor 240 included in the distance calculator 200 may be, for example, an IMU sensor. In addition, the distance calculator 200 may calculate the measurement distance E, which is a vertical distance between the distance sensor 220 and the object 500 located therebelow by substituting the spacing distance A and the tilt angle θ into a trigonometric function.

Meanwhile, the distance sensor 220 may measure a ground surface distance GL to the ground surface GL, and the distance calculator 200 may calculate the location distance D, which is the vertical distance between the distance sensor 220 and the ground surface GL, using the ground surface distance GL and the tilt angle θ. That is, the distance sensor 220 may measure a distance to the ground surface GL in a state in which no object 500 is present at the rear side, and may change the distance to a vertical distance via the trigonometric function. Thereby, the distance calculator 200 may calculate the location distance D between the distance sensor 220 and the ground surface GL. Alternatively, when the object 500 is present in a line behind the lower body mechanism 100, the distance calculator 200 may inversely calculate the location distance D in a mechanical manner using the lengths of the respective links and the angles of the respective joints of the lower body mechanism 100. To this end, the respective joints must be provided with means capable of measuring the angles of the joints.

Meanwhile, the controller 300 may control the drive devices of the lower body mechanism 100 so that the distance calculator 200 may move by the tolerance distance C when the measurement distance E is greater than the tolerance distance C. This serves to allow the lower body mechanism 100 to stably sit in a crouched posture even when the height of the object 500 is excessively low or when the lower body mechanism 100 sits on the ground surface GL because there is no object 500.

FIGS. 3 and 4 are views illustrating other sitting modes of the lower body supporting robot system illustrated in FIG. 1. When the measurement distance E, which is the distance from the distance calculator 200 to the object 500 or the ground surface GL, is greater than the tolerance distance C, which is the lowest height to which the lower body mechanism 100 may sit down, the lower body mechanism 100 may sit down only by the tolerance distance C due to mechanical restriction thereof. Accordingly, in this case, the controller 300 may control the lower body mechanism 100 so as to perform a predetermined sitting motion by the tolerance distance C, thereby assisting the user in stably crouching without applying strain to the lower body mechanism 100.

Meanwhile, FIG. 5 is a view illustrating a sitting mode of the lower body supporting robot system illustrated in FIG. 1 for an inclined object 500. The distance calculator 200 may be provided with a plurality of distance sensors 220, and may calculate measurement distances E1 and E2 using the respective distance sensors 220. The controller 300 may select the smallest measurement distance E1 among the measurement distances E1 and E2, may compare the smallest measurement distance E1 with the tolerance distance C, and may control the drive devices of the lower body mechanism 100 so that the distance calculator 200 may move by the smallest measurement distance E1 when the smallest measurement distance E1 is less than the tolerance distance C.

That is, when the sitting motion is implemented based on the calculation of the distance calculator 200 described above despite the fact that the surface of the object 500 is inclined as illustrated, a situation in which the system becomes unstable may occur because the lower body mechanism 100 collides with the object 500 or the sitting motion ends in a state in which the lower body mechanism 100 is not supported by the object 500. Therefore, in order to realize stable sitting even when the surface of the object 500 is not horizontal, the distance calculator 200 may include the distance sensors 220 so as to calculate the measurement distances E1 and E2 using the respective distance sensors 220. Then, the controller 300 selects the smallest measurement distance E1 among the measurement distances E1 and E2, compares the smallest measurement distance E1 with the tolerance distance C, and controls the drive devices of the lower body mechanism 100 so that the distance calculator 200 may move by the smallest measurement distance E1 when the smallest measurement distance E1 is less than the tolerance distance C. In this case, the lower body mechanism 100 may stably come into contact with the surface of the object 500 upon sitting.

FIG. 6 is a flowchart illustrating a control method of the lower body supporting robot system illustrated in FIG. 1. The method of controlling the lower body supporting robot system according to the present disclosure includes calculating the measurement distance E, which is the vertical distance between the distance calculator 200 and the object 500 located therebelow, calculating the location distance D, which is the vertical distance between the distance calculator 200 and the ground surface GL. The method further includes calculating, by the controller 300, the tolerance distance C, which is the difference between the location distance D and the limit distance B, and comparing, by the controller 300, the measurement distance E with the tolerance distance C and controlling the drive device of the lower body mechanism 100 so that the distance calculator 200 may move by the measurement distance E when the measurement distance E is less than the tolerance distance C.

In addition, as described above, in the calculation of the measurement distance E, the distance sensor 220 of the distance calculator 200 may measure the spacing distance A to the object 500 located therebelow, and the angle sensor 240 may measure the tilt angle θ between the distance sensor 220 and the ground surface GL, whereby the measurement distance E, which is the vertical distance between the distance sensor 220 and the object 500 located therebelow, may be calculated using the spacing distance A and the tilt angle θ.

In addition, in the calculation of the location distance D, the distance sensor 220 may measure the ground surface distance GL to the ground surface GL, whereby the location distance D, which is the vertical distance between the distance sensor 220 and the ground surface GL, may be calculated using the ground surface distance GL and the tilt angle θ. Alternatively, in the calculation of the location distance D, the location distance D may be calculated in a mechanical manner using the lengths of the respective links and the angles of the respective joints of the lower body mechanism 100.

As is apparent from the above description, according to a lower body supporting robot system, which is worn by a user who has paraplegia or other lower body disability in order to support movement of the lower body, and a control method thereof, it is possible to assist the user in stably sitting on an object in a sitting mode, and it is advantageous to secure the safety of the user without causing the user inconvenience by minimizing errors during a control operation, and a control method thereof.

Although embodiments of the present disclosure have been described above with reference to the accompanying drawings, those skilled in the art will appreciate that the present disclosure can be implemented in various other embodiments without changing the technical ideas or features thereof.

What is claimed is:

1. A lower body supporting robot system comprising:
a lower body mechanism being worn on a user's lower body, the lower body mechanism including a plurality of joints and links and a drive device;
a distance calculator provided above the lower body mechanism for measuring a first distance that is a vertical distance to an object located therebelow and a second distance that is a vertical distance to a ground surface;
a memory for storing a limit distance that is a vertical distance between the distance calculator and the ground surface in a state that the lower body mechanism is in a lowest sitting posture; and
a controller for calculating a tolerance distance that is a difference between the second distance and the limit distance, comparing the first distance with the tolerance distance, and controlling the drive device so that the distance calculator moves by the first distance when the first distance is less than the tolerance distance.

2. The lower body supporting robot system according to claim 1, wherein the links include a calf link and a thigh link, the joints include an ankle joint, a knee joint and a hip joint, and the drive device includes one or more drive devices for adjusting angles of the respective joints.

3. The lower body supporting robot system according to claim 1, wherein the distance calculator includes a distance sensor and an angle sensor,
wherein the distance sensor measures a spacing distance to the object located therebelow, and the angle sensor measures a tilt angle between the distance sensor and the ground surface, and
wherein the distance calculator calculates the first distance that is a vertical distance between the distance sensor and the object located therebelow using the spacing distance and the tilt angle.

4. The lower body supporting robot system according to claim 3, wherein the distance sensor measures a ground surface distance to the ground surface, and
wherein the distance calculator calculates the second distance that is the vertical distance between the distance sensor and the ground surface using the ground surface distance and the tilt angle.

5. The lower body supporting robot system according to claim 1, wherein the distance calculator calculates the second distance in a mechanical manner using lengths of the respective links and angles of the respective joints of the lower body mechanism.

6. The lower body supporting robot system according to claim 1, wherein the memory stores a motion rule of the drive device to be performed in a sitting mode, and
wherein the controller controls the drive device according to the motion rule when the lower body mechanism performs a sitting mode, and controls the drive device so that the distance calculator moves by the first distance when the first distance is less than the tolerance distance.

7. The lower body supporting robot system according to claim 1, wherein the controller controls the drive device of the lower body mechanism so that the distance calculator moves by the tolerance distance when the first distance is greater than the tolerance distance.

8. The lower body supporting robot system according to claim 1, wherein the distance calculator includes a plurality of distance sensors, and the distance sensors detect the first distances respectively,
wherein the controller selects a smallest distance among the first distances, compares the smallest distance with the tolerance distance and controls the drive device of the lower body mechanism so that the distance calculator moves by the smallest distance when the smallest distance is less than the tolerance distance.

9. A method of controlling the lower body supporting robot system according to claim 1, the method comprising:
- measuring the first distance that is the vertical distance between the distance calculator and the object located therebelow;
- measuring the second distance that is the vertical distance between the distance calculator and the ground surface;
- calculating, by the controller, the tolerance distance that is the difference between the second distance and the limit distance; and
- comparing, by the controller, the first distance with the tolerance distance, and controlling the drive device of the lower body mechanism so that the distance calculator moves by the first distance when the first distance is less than the tolerance distance.

10. The method according to claim 9, wherein, in the step of calculating the first distance, a spacing distance to the object located therebelow is measured using a distance sensor, and a tilt angle between the distance sensor and the ground surface is measured using an angle sensor, whereby the first distance that is a vertical distance between the distance sensor and the object located therebelow is calculated using the spacing distance and the tilt angle.

11. The method according to claim 10, wherein, in the step of calculating the second distance, a ground surface distance to the ground surface is measured using the distance sensor, whereby the second distance that is the vertical distance between the distance sensor and the ground surface is calculated using the ground surface distance and the tilt angle.

12. The method according to claim 10, wherein, in the step of calculating the second distance, the second distance is calculated in a mechanical manner using lengths of the respective links and angles of the respective joints of the lower body mechanism.

* * * * *